US009423346B2

(12) United States Patent
Xu

(10) Patent No.: US 9,423,346 B2
(45) Date of Patent: Aug. 23, 2016

(54) SYSTEM AND METHOD FOR HAZE MEASUREMENT

(71) Applicant: DATACOLOR HOLDING AG, Lucerne (CH)

(72) Inventor: Zhiling Xu, Princeton Junction, NJ (US)

(73) Assignee: DATACOLOR HOLDING AG, Luzern (CH)

( * ) Notice: Subject to any disclaimer, the term of this patent is extended or adjusted under 35 U.S.C. 154(b) by 54 days.

(21) Appl. No.: 14/213,064

(22) Filed: Mar. 14, 2014

(65) Prior Publication Data
US 2015/0260648 A1    Sep. 17, 2015

(51) Int. Cl.
*G01J 1/42*       (2006.01)
*G01N 21/59*      (2006.01)
*G01N 21/94*      (2006.01)
*G01N 21/47*      (2006.01)

(52) U.S. Cl.
CPC .......... *G01N 21/59* (2013.01); *G01N 21/4738* (2013.01); *G01N 21/94* (2013.01); *G01N 2021/4707* (2013.01); *G01N 2021/4735* (2013.01); *G01N 2021/4773* (2013.01); *G01N 2201/065* (2013.01); *G01N 2201/0633* (2013.01); *G01N 2201/0634* (2013.01); *G01N 2201/12746* (2013.01)

(58) Field of Classification Search
CPC .......... G01N 21/59–21/61; G01N 2021/8928; G01N 21/896; G01N 21/8901; G01N 21/958; G01N 21/47; G01N 21/474; G01N 21/8422; G01N 2201/065; G01N 21/94
See application file for complete search history.

(56) References Cited

U.S. PATENT DOCUMENTS

| 5,712,709 | A * | 1/1998 | Task et al. .................. 356/432 |
| 8,259,294 | B2 * | 9/2012 | Proehl et al. .............. 356/236 |
| 8,749,791 | B2 * | 6/2014 | Wimmer et al. ............ 356/445 |
| 2013/0050684 | A1 | 2/2013 | Wimmer et al. | |

* cited by examiner

*Primary Examiner* — Kara E Geisel
*Assistant Examiner* — Rufus Phillips
(74) *Attorney, Agent, or Firm* — Leason Ellis LLP.

(57) ABSTRACT

The present invention is directed to an apparatus and method for measuring the haze value of transmissive samples. The apparatus comprises a first light source selectively configurable to emit a first light beam, a second light source selectively configurable to emit a second light beam, an integrating sphere having an outer surface and an inner surface, the inner surface configured to reflect light incident upon the inner surface, the inner surface further enclosing an interior volume. The integrating sphere is further equipped with an exit port configured to emit light from the interior volume of the integrating sphere. The exit port is positioned such that light from the first light source exits the integrating sphere without obstruction, and light from the second light source is diffused on the interior surface of the integrating sphere prior to exiting the exit port. A light detector is also included and is configured to generate a light-intensity signal when light exiting the integrating sphere has passed through a sample and is incident on the light detector. The apparatus further includes a processor configured to receive the light-intensity signal and generate an output signal to a user indicating the haze value. The present invention is also directed to a method of calculating the haze value of a sample using a stored calibration value, a diffuse transmission value (sample-absent diffuse light-intensity value), a direct transmission value (sample-absent direct light-intensity value), a measured diffuse transmission value (sample-present diffuse light-intensity value) and a measured direct transmission value (sample-present direct light-intensity value).

20 Claims, 4 Drawing Sheets

SYSTEM AND METHOD FOR HAZE MEASUREMENT

FIELD OF THE INVENTION

The present invention is directed to a method and a system for measuring the haze value of light-transmitting samples in a convenient and faster way. The present invention uses multiple light sources and an integrating sphere to achieve reliable measurements of the haze value of a sample.

BACKGROUND OF THE INVENTION

The appearance of a transparent product is defined by how much light will pass through it and how objects will appear through the transparent product. Translucent products, such as for example glass, transparent sheets and the like, are used in many fields. In this case the optical properties play an important role, depending upon the field of application. In this way for example, a high degree of transmission is required of glass panels and sheets which are used for greenhouses. A sheet used for packaging, on the other hand, should allow the contents to be recognized as clearly as possible and with as little clouding as possible.

Devices for examining these optical properties are known in the art. Generally, such devices combine a light source to trans-illuminate a sample and a detector to detect this light once it has passed through the sample. Various analyses are performed to evaluate the conditions of the interior volume and surface conditions of the sample material that contribute to its transparency.

The appearance of an object is composed of many elements relating to the light absorption and scattering properties of the material under review. Transmission haze (or wide-angle scattering of light through a trans-illuminated sample) is a necessary measurement quantity that must be measured in order to ensure a uniform and consistent product. Furthermore, the haze characteristic of a sample is useful in analyzing pertinent process parameters and material properties, e.g. cooling rate or compatibility of raw materials.

Haze is considered that percentage of light which, in passing through a material, is deviated from its original path by more than 2.5 degrees on the average. Thus, haze provides a lack of distinctness of an image and contributes to an overall lack of clarity in a material. One way of measuring the transmission haze of a sample is to use an integrating sphere. An integrating sphere is a type of diffuse reflectance device. Light is directed into the interior volume of the integrating sphere, which is coated with a matte surface. The diffusion of light in the integrating sphere proceeds according to Lambertian behavior. This is distinct from specular reflectance which occurs on mirror-like surfaces. In an integrating sphere light is scattered and re-scattered inside the sphere until it escapes the sphere through an open port or is absorbed by the interior surface of the sphere. This multiple reflection causes the intensity of the light inside the sphere to be relatively constant at all points inside the sphere.

The article entitled Standard Test Methods for Haze and Luminous Transmittance of Transparent Plastics, ASTM D1003-07 (2008) hereby incorporated by reference, describes traditional methods of determining haze and luminous transmittance in transparent plastics. For example, a haze meter device is described which incorporates an integrating sphere designed to determine the angular distribution of the diffused portions of the light. In this device, light that has passed through the sample is attenuated by light loss through a selected circular aperture, which at the sample subtends an angle of 5 degrees. Alternatively, a spectrophotometer with an included integrating sphere is also described as suitable for use in determining the haze characteristics of the sample under measurement. In either device described in the standard, light that first scatters in the integrating sphere and passes through the sample reaches the light detector only if it is scattered from outside a selected circular aperture, which at the sample subtends an angle of 5 degrees. In both of these instances, the prior art devices were configured to measure light depletion due to use of only one size of port to constrain the angle of scattering from the sample. As a result, only haze is measured and not low-angle scattering. Haze characteristics such as wide angle scattering, are not easily measured. Even for haze measurement alone, four measurements are required for any evaluation of transmission haze, which variously involve a reflectance standard in/out of position, a light trap in/out of position, and a specimen in/out of position (see Section 7.2.1 in D1003). These measurements comprise incident light, total light transmitted by the sample, light scattered by the instrument, and light scattered by the instrument and sample.

In addition to this described standard method, there is also a further standard method according to the ISO. In the case of this further standard method the intention is also to take into consideration errors which occur as a result of change in efficiency—caused by the samples—of the Ulbricht sphere (integrating sphere) used. In this case for example single-beam methods are used, in which the sample to be investigated is applied to two different outlets of the Ulbricht sphere. In addition, double-beam methods are known, in which two light bundles are used, one constituting the measurement bundle which passes through the sample, and a further bundle which does not pass through the sample but illuminates the inner wall of the Ulbricht sphere. The last-named method has the drawback, however, that the aforesaid light bundles must be precisely attuned to each other and, in addition, influences from the background illumination (for example illumination of the space) should also be taken into consideration.

SUMMARY OF THE INVENTION

The present invention is directed to a system and method for measuring the haze value of light-transmitting samples. The system includes a first light source configurable to emit a first light beam, a second light source configurable to emit a second light beam, and an integrating sphere.

In one arrangement, the integrating sphere has at least one entrance port configured to introduce the first light beam into the interior volume, at least one second entrance port to introduce the second light beam into the interior volume, and at least one exit port configured to pass light out from the interior volume of the integrating sphere.

In an alternative arrangement, the integrating sphere has at least one entrance port configured to introduce a light beam from either the first or second light sources into the interior volume, the other light source is incorporated into the structure of the sphere (inside the sphere), and at least one exit port configured to pass light out from the interior volume of the integrating sphere.

In an alternative arrangement the integrating sphere has both light sources incorporated into the structure of the sphere (inside the sphere). In this arrangement, the integrating sphere is equipped with only a single exit.

Additionally, a light detector is configured to generate a signal when light is incident on the light detector. This arrangement is used to output data to a processor configured to evaluate the haze characteristics of a sample under an analysis based on the values of the light received by the light detector.

BRIEF DESCRIPTION OF THE DRAWINGS

The foregoing and other features of the present invention will be more readily apparent from the following detailed description and drawings of [an] illustrative embodiment[s] of the invention in which.

DESCRIPTION OF ILLUSTRATIVE EMBODIMENTS OF THE INVENTION

By way of overview and introduction, the present system and method provides testing instruments designed to achieve accurate measurement of the haze characteristics of a light-transmitting sample using multiple light sources and an integrating sphere. Specifically, the method and system of the present invention are configured to obtain accurate haze (wide angle-scattering) calibration values and accurate haze test values through the use of a variable-configuration light sources and integrating sphere.

The apparatus and system described provide a solution that enables technicians or other technical professionals to obtain more accurate haze measurement values. In particular arrangements of the elements of the invention described are used to determine both wide and narrow angle light scattering.

Those skilled in the art will appreciate that the device and method described herein can be modified to fit a number of design constraints. For example, in a particular arrangement of elements, the components of the illustrated device are constructed as a plurality of removable modules that are separately attached to one another by cables or conduits. These elements are configured to work in combination with other devices such as the Datacolor 600 Integrating-Sphere spectrophotometer of Datacolor Inc., Lawrenceville, N.J. The system and method described herein are also configured to operate as a separate independent device.

Figure 1:
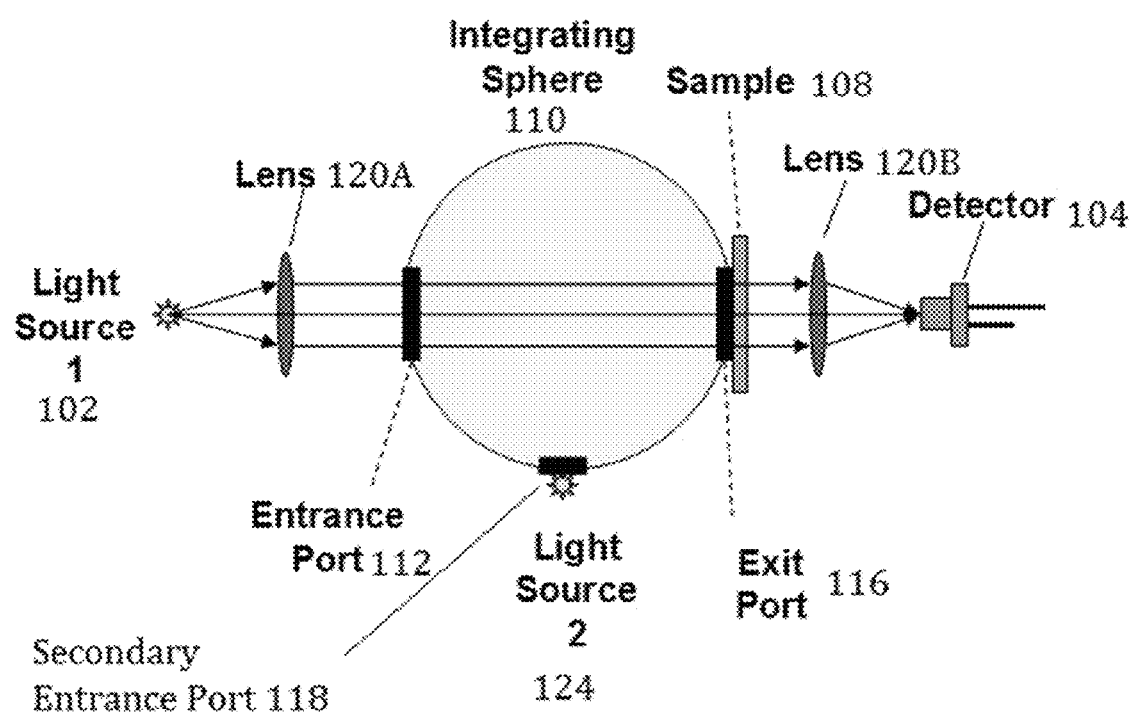
FIG. 1 is a schematic view of an embodiment of the present invention depicting the haze measurement apparatus.

As seen in FIG. 1, the illustrated arrangement of elements provides for a primary light source 102. The light source 102 is configured to direct a collimated light beam into an interior volume of an integrating sphere 110 through a primary light port 112. The light source 102, in one configuration, produces varying intensities of light depending on the specific testing parameters. In the illustrated arrangement, the light source 102 is a single, monochromatic LED lighting element. In alternative arrangements, the light source 102 may be a combination of monochromatic LEDs elements. In a further arrangement, the light source 102 may be comprised of a plurality of lighting elements, such as tungsten, xenon or fluorescent lighting elements. The light source 102 is configured to operate in a pulsed or continuous mode. In a given arrangement, the cycle for pulsed light directed into the integrating sphere is in the 10-1000 Hz range.

In a given arrangement, the light source(s) 102 incorporated in the illustrated arrangement has variable intensity depending on the testing parameters. In a particular arrangement, the intensity and frequency of the light source 102 is altered by a current limiting electrical circuit. In alternative arrangements the illumination and frequency of the light beam produced by the source 102 is controlled via programmable or non-programmable digital circuitry. In a further arrangement, the light source contains a plurality of lighting elements; each configured to produce a relatively stable light beam at a given frequency.

In the illustrated configuration, the light generated by the primary light source 102 is directed by a lens assembly 120A. The lens assembly 120A is configured to direct a collimated primary beam to the primary entrance port 112. The lens assembly 120A is formed of a standard instrument grade lens or lenses. The assembly is designed to be modular for ease of manufacture and repair. In a particular arrangement, the lens assembly is designed to place the plurality of lens elements in series so as to provide successive conditioning of a light beam so as to generate a collimated primary beam of a desired dimension or other characteristic.

In the illustrated arrangement, the light beam is directed inside the integrating sphere 110. The interior of the integrating sphere is coated with materials having a high diffuse reflectance value. For example, in one arrangement of materials, Spectralon®, Teflon® or a similar material is coated or applied to the interior of the integrating sphere 110. In another arrangement, the coating selected is configured to reflect 99% or greater of the incident light directed into the integrating sphere 110 in the wavelengths from 300 nm to 900 nm. In the alternative, the interior of the integrating sphere is coated with a barium sulfate based paint which possess a lower reflective relative to Spectralon®.

In the illustrated embodiment, the integrating sphere 110 is equipped with a primary entrance port 112, a secondary entrance port 118, and an exit port 116. In the described arrangement, the exit port 116 is aligned with the primary entrance port 112. In this configuration, the collimated main beam generated by the primary light source 102 travels unimpeded through the integrating sphere 110 and exits the integrating sphere through the exit port 116.

In an alternative arrangement, the integrating sphere 110 has at least one entrance port 112 configured to introduce a light beam from either the first or second light sources into the interior volume, the other light source is incorporated into the structure of the sphere (inside the sphere), and at least one exit port 116 configured to pass light out from the interior volume of the integrating sphere.

In an alternative arrangement the integrating sphere 110 has both light sources incorporated into the structure of the sphere (inside the sphere). In this arrangement, the integrating sphere is equipped with a single exit 116.

In the illustrated arrangement, the dimensions of the ports described are all roughly equivalent. However, those skilled in the art will appreciate that maintaining the relative size of the primary light port 112, as compared to the secondary light entrance port, is not necessary. In an alternative construction, the primary light port 112 is configurable to expand or contract its diameter depending on type of primary light source 102.

In one configuration, the exit port 116 is configured to allow light that has passed through the integrating sphere 110 unimpeded to travel to a light detector or sample channel sensor 104. In another configuration, a sample 108 is secured adjacent to the exit port 116. In this configuration, light that has passed unimpeded through the integrating sphere 110 is incident upon the sample, and is transmitted through the sample to the sample channel sensor 104. The sample 108 can also be a standard with known haze value for calibration.

In one configuration, a secondary lens assembly 120B is positioned between the exit port 116 and the sample channel sensor 104. Alternatively, in another configuration, the secondary lens assembly is positioned between the sample or calibration standard 108 and sample channel sensor 104. In a particular arrangement, the secondary lens assembly is formed of a standard instrument grade lens or lenses. The assembly is designed to be modular for ease of manufacture and repair. In a particular arrangement, the lens assembly 120B is formed of a plurality of lens elements. When combined, each element of the secondary lens assembly is designed to cooperate with one another so as to focus incoming light at a focal point. For example, the light is focused by the secondary lens elements so as to converge at a focal point coinciding with the sample channel sensor 104.

As seen in FIG. 1, the illustrated arrangement of elements provides for a secondary light source 124. The secondary light source 124 is configured to direct a light beam into an interior volume of the integrating sphere 110 through the secondary light port 118. The light source 124, in one configuration, produces varying intensities of light depending on the specific testing parameters. In the illustrated arrangement, the secondary light source 124 is a single, monochromatic LED lighting element. In alternative arrangements, the secondary light source 124 may be a combination of monochromatic LEDs elements. In a further arrangement, the secondary light source 124 may be comprised of a plurality of lighting elements, such as tungsten, xenon or fluorescent lighting elements. The secondary light source 124 is configured to operate in a pulsed or continuous mode. In a given arrangement, the cycle for pulsed light directed into the entrance port 118 of the integrating sphere is in the 10-1000 Hz range.

When the light from the secondary light beam 124 is directed into the interior of the integrating sphere 110, it is diffused on the coated inner surface of the integrating sphere 110. The light from the secondary light source 124 is continuously dispersed around the interior volume of the integrating sphere 110. The dispersed light is diffused such that only light that has been reflected off the interior walls is capable of leaving the interior volume of the integrating sphere 110 through the exit port 116. Once the diffused light has left the integrating sphere 110; it either passes directly to the sample channel sensor 104 or first passes through the volume of the sample 108 prior to being incident on the sample channel sensor 104.

In one configuration, the primary light source is activated and deactivated prior to activating the secondary light source. In an alternative, both the primary and secondary light sources are activated, but at least one shutter, shade or other light obscuring device is inserted to interrupt either the beam generated by the primary light source or secondary light source from entering the integrating sphere. In a further configuration, the primary and secondary light sources are pulsed so as to allow alternating periodic active and deactivated states during the course of sample measurement.

In the illustrated arrangement of FIG. 1, the lens assembly 120B is configured to focus light transmitted through the volume of the sample 108 to a focal point where the sample channel sensor 104 is positioned. The sample channel sensor 104 is an industry standard sensor designed to accurately measure the intensity and fluctuation of the light source 102. In a particular construction, the sample channel sensor 104 is a silicon photodiode or photomultiplier tube configured to be sufficiently sensitive so as to determine the intensity level of light that has passed through a sample 108. In another arrangement, the sample channel sensor 104 functions by producing an output that is linearly related to the intensity of the received illumination when the illumination intensity is below a given threshold.

Figure 2:
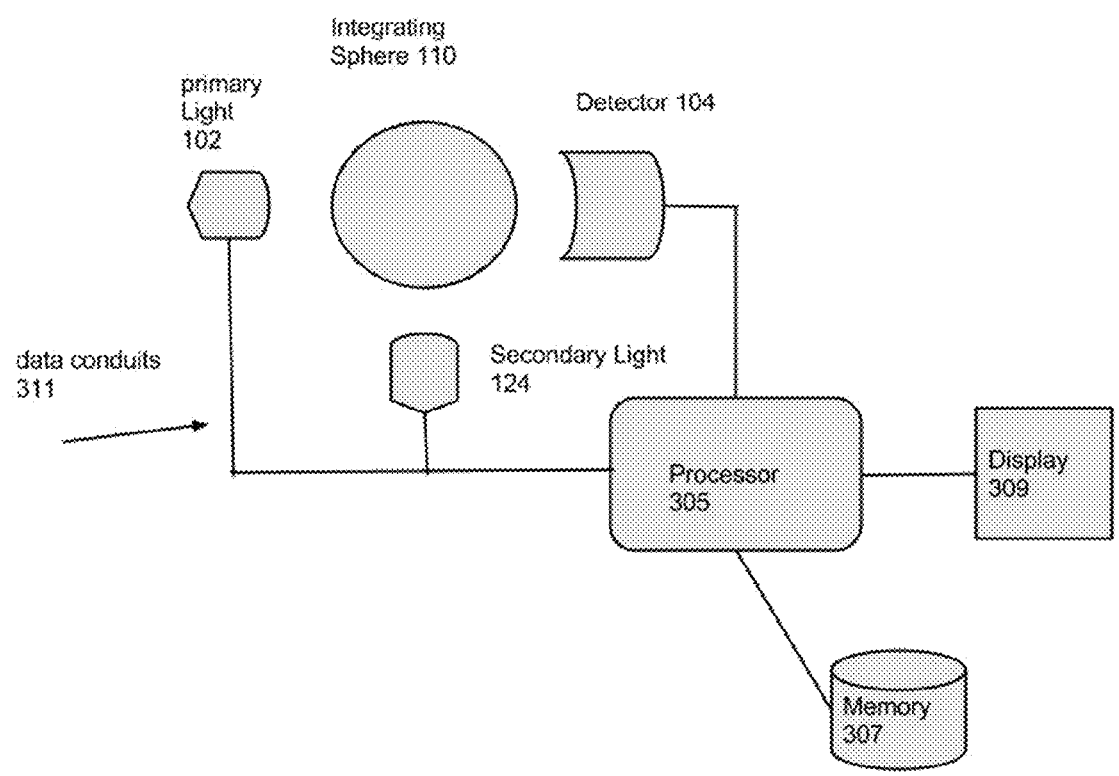
FIG. 2 is a schematic view of the elements of the present invention depicting the haze measurement apparatus.

The sample sensor 104 is equipped with sufficient circuitry to allow for the output of the sensing element to be known or interpreted by a data logging or processing system 305 as shown in FIG. 2. Furthermore, the sample channel sensor 104 is configured such that in the event that the sensor element is saturated (i.e. the illumination incident upon the sensor element exceeds the element sensing threshold) the sample channel sensor 104 is configured to output a maximum value corresponding to the acceptable value indicating maximum illumination. In this situation, the sample channel sensor 104 output no longer tracks changes in the input without further correction. However, even at saturation, the sensor 104 will continue to respond to input signals. Thus, measurements obtained above the saturation threshold will not have true values. However, the values relative to the sensing element will still be output from sensor 104 to a processor or computer 305 configured to receive the data or signals output from the sensor(s).

Likewise, the sample channel sensor 104, in one arrangement, is also equipped with a diffraction grating (not shown) which allows for the analysis of light transmitted through the sample and received by the sample channel sensor 104. The diffraction grating configures light into its spectral components for a detailed analysis of each specific wavelength component. In this way, the correction of the flash to flash deviations is accomplished using comparisons specific to each wavelength component. Thus, a more precise correction of the light intensity deviation is achieved.

In the illustrated arrangement of elements, it is understood that the ambient light outside of the integrating sphere 110 is at a level of intensity that does not significantly alter the illumination intensity detected by the sensor 104. However, in an alternative arrangement, a light trap, or baffle (not shown) is configured to prevent ambient light from entering the integrating sphere 110 when one or both light ports are not in active use.

It should be noted that the sample sensor is configured by the system to operate within an optimal range of illumination value. When the measurement falls below this range, the signal to noise ratio of the measurement renders the output signal undesirable. Likewise, if the illumination intensity is too high, the sensor becomes saturated and fails to provide an accurate reading.

In a measurement operation, when the light from the primary light source 102 is directed through the integrating sphere 110, a column of light measuring the dimensions of the exit port 116 will strike the sample 108 and be directed to the sample channel sensor 104. In this configuration, the sample is secured by a sample holder (not shown). In an alternative arrangement, the sample holder includes a plurality of samples. In this configuration, the samples are moved automatically into a position for intercepting the light beam generated by the primary or secondary light sources. Once a satisfactory measurement of the light from the primary light source 102 has been obtained, the primary light source is deactivated. The secondary light source 124 is activated. Only secondary light that has at least undergone diffusion by striking the interior of the integrating sphere 110 and has been transmitted through the sample 108, reaches the sample channel sensor 104. In one operation step, the sample is removed from its position adjacent to the exit port 116. In another operation step, the sample is put back and sample measurements of the primary light source and the secondary light source are obtained by the sensor 104.

As seen in FIG. 2, a processor 305 is configured to determine the amount of illumination incident upon the sensor 104. The processor (or computer) 305 is configured (e.g. by instructions executing therein) to generate a data model having a relation to the haze characteristics of the sample 108. The computer or processor 305 is connected to the sensor 104 through communication conduits 311. These conduits permit the bi-directional transmission of information and control data between the sensor 104 and the processor 305. Additionally, the processor is configured to control or monitor the activation, intensity or other characteristics of the primary and secondary light sources (102, 124). The data generated by the sensor 104 is transmitted by the conduits to the processor 305 in order to determine the haze characteristics of the sample 108, using widely understood algorithms.

In ASTM D1003, haze is calculated according to Formula 1 as provided below.

$$\text{haze} = \frac{T_d}{T_t} \times 100\% = \left(\frac{T_4}{T_2} - \frac{T_3}{T_1}\right) \times 100\%. \quad (1)$$

In the single-light-source instruments described in ASTM D1003, the quantities $T_1$-$T_4$ can be either light intensities or transmittance values. Because there are multiple light sources in the current invention, it is necessary to commit to an interpretation of quantities T as either light intensities or transmittance values. As used herein, the T values are defined as transmittance values (which are dimensionless).

Accordingly, in the current description, $T_1$ corresponds to the total transmittance value without the sample inserted in between the integrating sphere and the light sensor. $T_2$ is total transmittance value with the sample inserted in between the integrating sphere and the light sensor. $T_3$ is diffuse transmittance value without the sample placed in between the integrating sphere and the light sensor. $T_4$ is diffuse transmittance value with the sample placed. Using the above convention, $T_5$ represents the regular (or direct) transmittance value without the sample placed in between the integrating sphere and the light sensor. Likewise, $T_6$ represents the regular transmittance value with the sample placed in between the integrating sphere and the light sensor.

Those skilled in the art will appreciate that $T_1=T_3+T_5$ and $T_2=T_4+T_6$. Thus, $$\text{haze} = \left(\frac{T_4}{T_2} - \frac{T_3}{T_1}\right) \times 100\% = \left(\frac{T_4}{T_4+T_6} - \frac{T_3}{T_3+T_5}\right) \times 100\% \quad (2)$$

The use of Eq. 2 requires further elaboration, because the quantities T are not directly measured. Indeed, each quantity T is a ratio whose numerator is a light intensity I sensed by the instrument sensor 104 (with sample either in or out), and whose denominator is a total flux S of one of the lights through the exit aperture. Accordingly, $$T_3 = \frac{I_3}{S_2} \cdot k_2$$

$$T_4 = \frac{I_4}{S_2} \cdot k_2$$

where $S_2$ is the total flux power of light source 2 through the exit aperture that is used to measure diffuse transmission, $I_3$ is the light intensity measured by the detector without sample in the light path, $I_4$ is the light intensity measured by the detector with sample in the light path, and $k_2$ is a coefficient associated with diffuse transmission.

Similarly, $I_5$ and $T_6$ can be calculated as:

$$T_5 = \frac{I_5}{S_1} \cdot k_1$$

$$T_6 = \frac{I_6}{S_1} \cdot k_1$$

where $S_1$ is the total flux of light source 1 through the exit aperture that is used to measure regular transmission, $I_5$ is the light intensity measured by the detector without sample in the light path, $I_6$ is the light intensity measured by the detector with sample in the light path, and $k_1$ is a coefficient associated with regular (i.e., direct) transmission.

Given the above substitutions, the haze values desired can be calculated according to the following, $$\text{haze} = \left(\frac{T_4}{T_4+T_6} - \frac{T_3}{T_3+T_5}\right) \times 100\%$$

$$= \left(\frac{\frac{I_4}{S_2} \cdot k_2}{\frac{I_4}{S_2} \cdot k_2 + \frac{I_6}{S_1} \cdot k_1} - \frac{\frac{I_3}{S_2} \cdot k_2}{\frac{I_3}{S_2} \cdot k_2 + \frac{I_5}{S_1} \cdot k_1}\right) \times 100\%$$

$$= \left(\frac{I_4}{I_4 + \frac{k_1 \cdot S_2}{k_2 \cdot S_1} \cdot I_6} - \frac{I_3}{I_3 + \frac{k_1 \cdot S_2}{k_2 \cdot S_1} \cdot I_5}\right) \times 100\%$$

A coefficient k can be defined as $$k = \frac{k_1 \cdot S_2}{k_2 \cdot S_1}.$$

Thus the haze value need to be expressed in terms of only the measurements $I_3$, $I_5$, $I_4$, and $I_6$ and one undetermined constant k, as follows $$\text{haze} = \left(\frac{I_4}{I_4 + k \cdot I_6} - \frac{I_3}{I_3 + k \cdot I_5}\right) \times 100\% \quad (3)$$

Note that, given knowledge of the constant k, Eq. (3) allows computation of haze from only values I, with no need to measure quantities S.

Those skilled in the art will appreciate that there are a variety of ways to determine the value k using a calibration process. In one example, the value k is determined by using a material standard with a known haze value, and measuring a set of values $I_3$, $I_4$, $I_5$, $I_6$, and calculating k from Eq. 3 by solving Eq. 3 for k (which, upon rationalizing the denominators, is a quadratic equation).

In the alternative, in a circumstance when there are multiple material standards with known haze values available, the calibration process includes measuring a set of values $I_3$, $I_4$, $I_5$, $I_6$ for each one of the multiple materials and calculating k through non-linear regression algorithm.

In a further arrangement, the calibration process includes adjusting the relative values of $S_1$ and $S_2$ (such as manually or through software calibration techniques) so that for a known haze calibration standard, the coefficient k=1, then the haze value of any sample can be directly obtained as $$\text{haze} = \left(\frac{I_4}{I_4 + I_6} - \frac{I_3}{I_3 + I_5}\right) \times 100\% \quad (4)$$

After calibration, the haze value of any sample can be directly obtained by measuring its corresponding values of $I_3$, $I_4$, $I_5$, $I_6$ and calculating with equation (3).

$$\text{haze} = \left(\frac{I_4}{I_4 + k \cdot I_6} - \frac{I_3}{I_3 + k \cdot I_5}\right) \times 100\%$$

In fact, for a given setup, $I_3$ and $I_5$ only need to be measured once, and for each following sample, only $I_4$ and $I_6$ need to be measured in order to get its haze value.

In the described system, once a calibration measurement is obtained different haze samples can be directly loaded and measured without further calibration. In one further configuration, the different haze samples are arranged to be automatically inserted and withdrawn from the measurement position between the exit port 116 and the lens assembly 120B. For example a batch processing mechanism is employed that contains a large compliment of samples. This makes the haze measurement more convenient and much quicker.

The processor 305, through the use of the above algorithm, or a suitably modified algorithm, is able to calculate the haze characteristics of the sample. In part, this is accomplished by allowing the processor 305, through the conduits 311, to control the activation state and intensity of the primary and secondary light sources 102 and 124. This data model is stored in a database 307 and subsequently presented to a user, through an output device 309 as an audio-visual display or data table.

The processor 305 is also configurable to interpret the data generated from the sensor 104 and use it to generate data models regarding the total transmittance conditions of the sample. For instance, the computer 305 is equipped to perform statistical analysis like least square fit optimizations, and/or similar computational analysis on the resulting data so that the variations of illumination are properly compensated. In a further arrangement these compensations algorithms employ the use of data obtained from a reference channel (not shown). Those skilled in the art will appreciate the various computational mechanisms available to computer 305 for obtaining data values from data channel outputs of the sensor. In a further arrangement, the processor 305 is configured to output a haze value to a user. In a further arrangement, the processor is configured to have a pre-set threshold value for haze characteristics. In the event that the sample under analysis exceeds the threshold value, an alarm or trigger, such as an audio-visual indicator, is directed to a user or to a remote analysis station.

Figure 3:
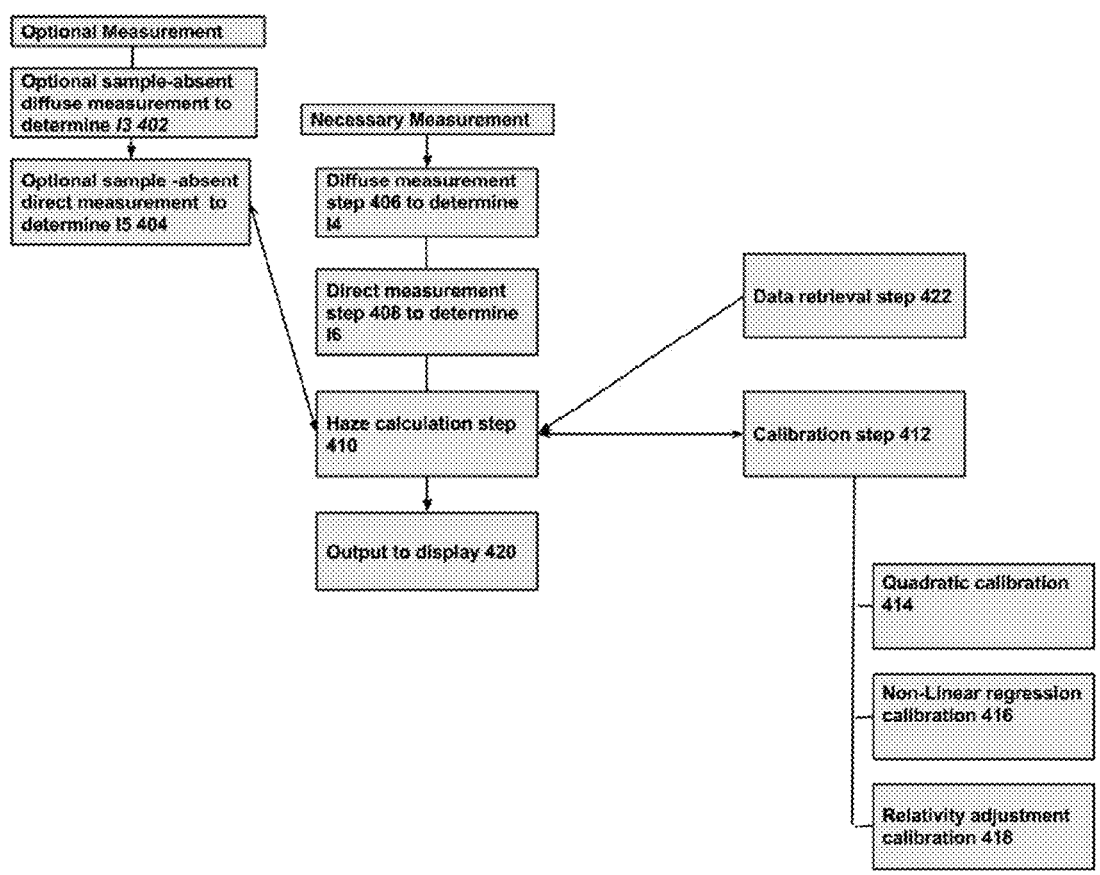
FIG. 3 is a flow chart describing the process of obtaining an accurate haze measurement steps described in FIG. 1.

As provided in FIG. 3, the present invention also incorporates a method of using the system described to carry out and achieve the function of generating a data model relating to the haze properties of a sample. Such a method involves a diffuse measurement stage and a regular measurement stage. An optional calibration stage is also provided. Both the diffuse and regular measurement stages must be carried out when calibrating (determining the k value provided in Equation 3) and when measuring a test sample.

The method includes optional sample-absent diffuse and direct measurement stages when there are no previous stored values relating to $I_3$ and $I_5$, or when a k values needs to be determined.

The optional sample-absent diffuse measurement step 402, in the event that a measured value $I_3$ has not previously been obtained, includes obtaining a signal generated by the sensor corresponding to the sample-absent diffuse transmitted-light-intensity value (herein also called a sample-absent diffuse transmission value) $I_3$ measured by the detector of light diffused on the interior of the integrating sphere without a sample in the light path, as measured by the sensor 104. If the $I_3$ value was previously measured, it is accessed from a storage device at the time of haze calculation.

An optional sample-absent direct measurement stage 404 involves, in the event that a measured value $I_5$ has not previously been obtained, obtaining a signal corresponding to the sample-absent direct transmitted-light-intensity value (herein also called a sample-absent direct transmission value) $I_5$ measured by the detector of light that has passed through the integrating sphere unimpeded without a sample in the light path, as measured by the sensor 104. If the $I_5$ value was previously measured, it is accessed from a storage device at the time of haze calculation.

For example, in one arrangement of the described method includes a data accessing step 422 for retrieving k, $I_3$ and $I_5$ values from a memory or database. In this arrangement, the data retrieval step 422 includes accessing a memory storage device and transmitting stored data to the processor for calculation.

Each of the potential arrangements includes a diffuse measurement step 406 that includes diffusing light on the interior of the integrating sphere, that light exiting the sphere and traveling through a sample to the sensor 104. A signal, corresponding to the diffuse transmitted-light-intensity value (herein also called a diffuse transmission value) $I_4$ measured by the detector with a sample in the light path, is generated by the sample sensor 104 and accessible by the processor 305.

Each of the potential arrangements further includes a direct measurement step 408, that includes directing a collimated light beam to the integrating sphere 110. The light exits the sphere unimpeded and is transmitted through the sample to the sensor 104. A signal corresponding to the direct transmitted-light-intensity value (herein also called a direct transmission value) h is measured by the sensor 104 and accessible by the processor 305.

A calculating step 410 is provided where the $I_3$, $I_4$, $I_5$ and $I_6$ values are used to obtain the haze value according to Eq. 3, repeated below:

$$\text{haze} = \left(\frac{I_4}{I_4 + k \cdot I_6} - \frac{I_3}{I_3 + k \cdot I_5}\right) \times 100\%$$

The method also includes an optional calibration step 412 to determine the coefficient k, when the value k is not known or accessible from a data storage device. The calibration step 412 includes selecting one of a plurality of sub-steps, based on the conditions present, in order to calculate the k value.

In one arrangement of the calibration step 412 includes a quadratic calculating step 414, that uses a material standard with a known haze value, the measured values $I_3, I_4, I_5, I_6$, (by directly obtaining the values as in steps 402, 404, 406 and 408) to calculate k from Eq. 3 by solving Eq. 3 for k (which, upon rationalizing the denominators, is a quadratic equation).

A second alternative optional sub-step 416 includes obtaining material standards values with known haze values available, and measuring a set of values $I_3, I_4, I_5, I_6$ for each one of the multiple materials and calculating k through a non-linear regression algorithm.

A third alternative optional sub-step 418 includes adjusting the relative values of $S_1$ and $S_2$ (such as manually or through software techniques) so that for a known haze calibration standard, the coefficient k=1, then the haze value of any sample can be directly obtained as $$\text{haze} = \left(\frac{I_4}{I_4 + I_6} - \frac{I_3}{I_3 + I_5}\right) \times 100\% \quad (4)$$

After calibration, the haze value of any sample can be directly obtained by inputting the values of $I_3, I_4, I_5, I_6$ into equation (3).

As provided above, $I_3$ and $I_5$ need to be measured as part of the calibration stage 412. For each subsequent sample measurement, only $I_4$ and $I_6$ need to be measured directly in order to get its haze value.

Those skilled in the art will recognize that data storage and event logging steps are inherent to those measurement steps described. The method also provides for an analysis step where a processor receives the stored values and generates a model of the haze properties of the sample.

Figure 4:
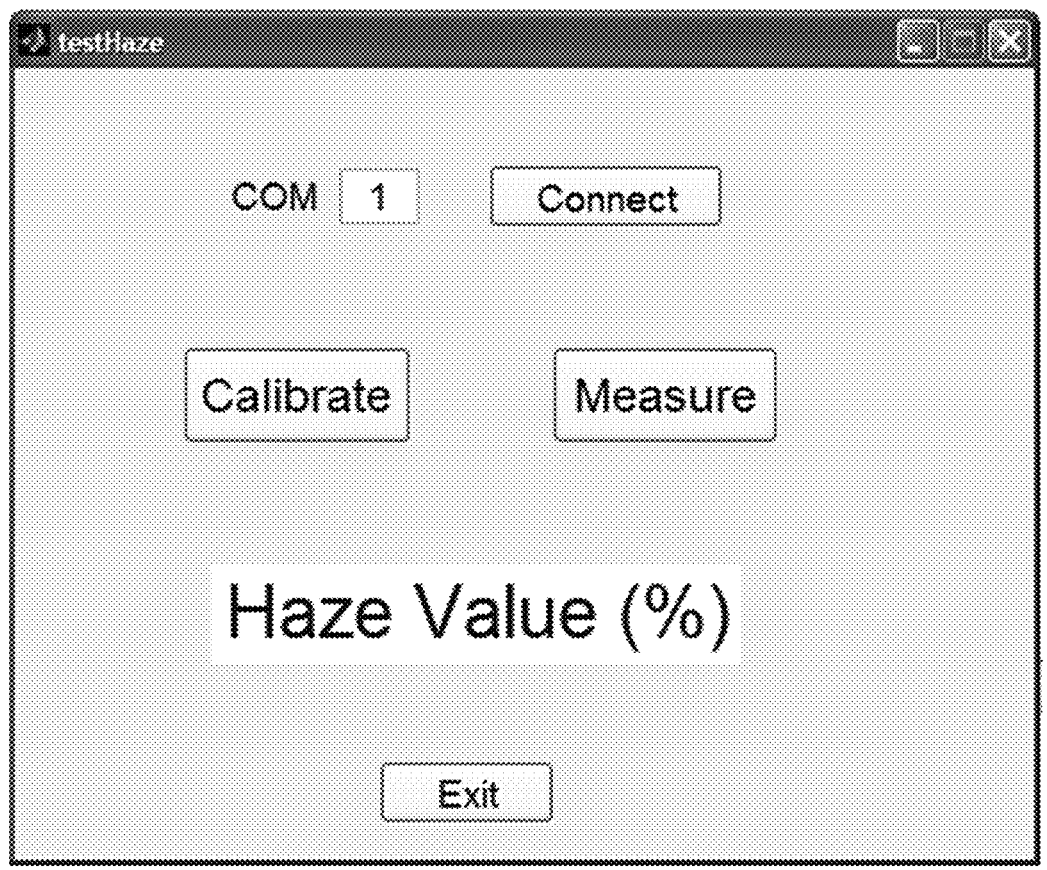
FIG. 4 is a view of the output information generated by the invention described.

Next, an output step 420 is provided where the haze data model is transformed into an audio-visual indications, providing the user with information regarding the direct and diffuse transmittance properties of the sample as shown in FIG. 4.

The steps described above and each of their processing functions can be operated as a series of programmed steps performed by a computer system having a processor or processors configured using one or more modules of computer-executable code. For instance, a set of software modules can be configured to cooperate with one another to configure a processor so that when executed, they provide accurate direct and diffuse transmittance information to a display device as described herein. In this regard, there can be a plurality of measuring modules, an analysis module, a calculation module and an output module.

Each measuring module can be configured as a series of discrete sub-modules designed to access and control the sensor data and configure the resulting signals generated from the sensor elements for output to the calculation module or analysis module for storage or manipulation.

A calculation module can be configured as a series of discrete sub-modules designed to access the data structures generated by the measuring module and correlate that data to the specific volumetric conditions of the sample. For example, the calculation module can be configured to determine the relative clarity of the sample and the nature of the light incident upon the sample channel sensor.

An analysis module can be configured as a series of discrete sub-modules designed to compare the data structures generated by the measuring module and provide comparison analysis to stored baseline readings. Furthermore, the analysis module is capable of performing statistical analysis functions on the data structures to determine the extent of the variations in the intensity of the light directed through the sample.

An output module is provided where the result of the calculation module and the analysis module are transformed into audio-visual information for use in a display or audio-visual indication.

A testing module, where the results of the calculation module are compared to a stored reference value or range of values and a user perceptible indicator, is activated in the event that the results of the calculation are outside the range of stored values.

Each of these modules can comprise hardware, code executing in a processor, or both, that configures a machine, such as the computing system, to implement the functionality described herein. The functionality of these modules can be combined or further separated, as understood by persons of ordinary skill in the art, in analogous implementations of arrangements of the invention.

It should be understood that various combination, alternatives and modifications of the present invention could be devised by those skilled in the art. The present invention is intended to embrace all such alternatives, modifications and variances that fall within the scope of the appended claims. While the invention has been particularly shown and described with reference to a preferred arrangement thereof, it will be understood by those skilled in the art that various changes in form and details may be made therein without departing from the spirit and scope of the invention.

What is claimed:

1. An apparatus for measuring the haze value of transmissive samples, the apparatus comprising:
a first light source selectively configurable to emit a first light beam,
a second light source selectively configurable to emit a second light beam,
an integrating sphere having an outer surface and an inner surface, the inner surface configured to reflect light incident upon the inner surface, the inner surface further enclosing an interior volume, the integrating sphere is equipped with at least one entrance port configured to allow light from one of the light sources to enter the integrating sphere the integrating sphere having an exit port configured to emit light from the interior volume of the integrating sphere, wherein the exit port is positioned such that light from the first light source exits the integrating sphere without obstruction, and light from the second light source is diffused on the interior surface of the integrating sphere prior to exiting the exit port;
a light detector configured to generate a signal when light that has left the exit port of the integrating sphere is incident on the light detector, and
a processor configured to activate only the first light source and receive the signal generated by the light detector and activate only the second light source and receive the signal generated by the light detector and calculate a haze value based on the signals generated by the light detector such that $$\text{haze} = \left(\frac{I_4}{I_4 + k \cdot I_6} - \frac{I_3}{I_3 + k \cdot I_5}\right) \times 100\%;$$

wherein k is a stored calibration coefficient value, $I_3$ corresponds to a first measurement made by the light detector with the second light source activated and a sample located between the exit port and the light detector, $I_5$ is a first measurement value with the first light source activated and a sample located between the exit port and the light detector, $I_4$ is a second measurement value with the second light source activated and no sample is located between the exit port and the light detector, and $I_6$ is a second measurement value with the first light source activated and no sample located between the exit port and the light detector direct transmission value.

2. The apparatus for measuring the haze value of a sample as in claim 1 wherein, The integrating sphere is equipped with at least a first and second entrance port, respectively configured to allow light from the first and second light sources to enter the first and second entrance ports of the integrating sphere.

3. The apparatus for measuring the haze value of a sample as in claim 1 further comprising,
at least one lens positioned between the first light source and the interior of the integrating sphere and at least one lens positioned between the exit port and the light detector.

4. The apparatus for measuring the haze value of a sample as in claim 1,
wherein the processor is further configured to connect to an alarm and a database, wherein the alarm is activated by a trigger signal generated by the processor.

5. The apparatus for measuring the haze value of a sample as in claim 4,
wherein the database is configured to store a range of haze measurement reference values.

6. The apparatus for determining the set of haze values as in claim 5,
wherein the processor is further configured to compare the stored reference values with sample derived haze measurement values, and to generate the trigger signal to activate the alarm when the derived haze measurement values are outside of the range.

7. The apparatus for determining the set of haze measurement values as in claim 3,
wherein the primary light source is equipped with a light tube configured to direct and focus light output traveling along the axis of the light tube through the integrating sphere.

8. The apparatus for determining the set of haze measurement values as in claim 1,
wherein the primary light source and secondary light source are arranged at right angles to one another.

9. The apparatus for determining the set of haze measurement values as in claim 1,
further including a sample holder configured to retain a sample under analysis positioned between the exit port of the integrating sphere and the light detector.

10. The apparatus for determining the set of haze measurement values as in claim 7,
wherein the sample holder includes a plurality of samples.

11. The apparatus for determining the set of haze measurement values as in claim 10,
wherein the sample holder is configured to automatically advance one of the plurality of samples to a position between the exit port and the light detector based on a signal from the processor.

12. A computer-implemented method for utilizing a particular connection with an electronic device in determining a set of haze characteristics of a sample using at least one light detection device, an integrating sphere having an interior surface and configured to enclose a given volume, at least a primary and secondary configurable light sources, the particular electronic device having a processor, a memory, an input device, an output device and a calculation application stored in the memory and executable by the processor, the method comprising the steps of:
projecting a first light beam from the primary light source into an integrating sphere, the light beam positioned so as to not interact with the interior surface of the integrating sphere;
measuring the first light output from an exit port of the integrating sphere with a light detecting device;
projecting a second light beam from the secondary light source onto an interior surface of the integrating sphere so as to generate a diffuse transmitted-light-intensity value (herein also called a diffuse transmission value) related thereto;
measuring the second light output from the exit port with the light detector device;
inserting a transmissive sample between the exit port of the integrating sphere and the light detection device;
projecting a third light beam from the primary light source into the integrating sphere and the transmissive sample being positioned outside the integrating sphere and the first light beam being positioned so as to pass unobstructed through the integrating sphere;
measuring the third light output from the exit and incident on the light detector device and generating a second direct transmission value;
projecting a fourth light beam from the secondary light source into the second entry port of the integrating sphere and onto an interior surface of the integrating sphere;
measuring the fourth light output from the exit and incident on the light detector device and generating a second diffuse transmission value;
calculating a haze value of the sample such that $$\text{haze} = \left(\frac{I_4}{I_4 + k \cdot I_6} - \frac{I_3}{I_3 + k \cdot I_5}\right) \times 100\%;$$

wherein k is a stored calibration coefficient value, $I_3$ is the first diffuse transmission value, $I_5$ is the first direct transmission value, $I_4$ is the second diffuse transmission value and $I_6$ is the second direct transmission value, and
outputting an audio-visual indicator correlated to the haze value of the sample.

13. A computer implemented method of measuring the haze value of a sample as in claim 12, further including:
computing a calibration value k for a calibration material having a known haze value such that $$\text{haze} = \left(\frac{I_4}{I_4 + k \cdot I_6} - \frac{I_3}{I_3 + k \cdot I_5}\right) \times 100\%;$$

wherein $I_3$ is the first diffuse transmission value, $I_5$ is the first direct transmission value, $I_4$ is the second diffuse transmission value and $I_6$ is the second direct transmission value.

14. A computer implemented method of measuring the haze value of a sample as in claim 12, further including:

computing a calibration value k for a plurality of calibration materials having a known haze values such that for each calibration material the $I_3$, $I_4$, $I_5$, and $I_6$ values are measured and used to calculate k using a non-linear regression algorithm, wherein $I_3$ is the first diffuse transmission value, $I_5$ is the first direct transmission value, $I_4$ is the second diffuse transmission value and $I_6$ is the second direct transmission value.

15. A computer implemented method of measuring the haze value of a sample as in claim 12, further including:
wherein the calculation step includes a determining calibration value k for a calibration material having a known haze value by adjusting the relative intensity of the diffusing light and the direct light such that the haze calibration value k becomes k=1; and
calculating the haze value according to the formula $$\text{haze} = \left(\frac{I_4}{I_4 + I_6} - \frac{I_3}{I_3 + I_5}\right) \times 100\%.$$

16. A computer implemented method of measuring the haze value of a sample as in claim 13, where the calculating step includes:
computing a haze value of the sample such that $$\text{haze} = \left(\frac{I_4}{I_4 + k \cdot I_6} - \frac{I_3}{I_3 + k \cdot I_5}\right) \times 100\%$$

wherein $I_3$ is the first diffuse transmission value, $I_5$ is the first direct transmission value, $I_4$ is the second diffuse transmission value and $I_6$ is the second direct transmission value.

17. A computer implemented method of measuring the haze value of a sample as in claim 12, further including a step of,
introducing at least one lens element between the first light source and the entry port of the integrating sphere and at least one lens element between the exit port of the integrating sphere and the light detection device.

18. A computer implemented method of measuring haze as in claim 14 where:
the activation state of the first and second light sources is controlled automatically in response to a signal generated by the processor.

19. A computer implemented method of measuring haze as in claim 12 where:
the sample is positioned between the exit port and the detector device automatically in response to a signal generated by the processor.

20. A computer implemented method of measuring the haze value of a sample as in claim 16, where the calculating step further includes:
computing a haze value according to the formula $$\text{haze} = \left(\frac{I_4}{I_4 + k \cdot I_6} - \frac{I_3}{I_3 + k \cdot I_5}\right) \times 100\%,$$

wherein k is a stored calibration coefficient value, $I_3$ is a diffuse transmission value (sample-absent diffuse light-intensity value), $I_5$ is a direct transmission value (sample-absent direct light-intensity value), $I_4$ is the measured diffuse transmission value (diffuse light-intensity value) and $I_6$ is the measured direct transmission value (direct light-intensity value).

* * * * *